United States Patent
Kawaguchi et al.

(10) Patent No.: US 9,637,584 B2
(45) Date of Patent: *May 2, 2017

(54) METHOD FOR PRODUCING POLYTHIOL COMPOUND, POLYMERIZABLE COMPOSITION FOR OPTICAL MATERIAL, AND USES THEREOF

(71) Applicant: MITSUI CHEMICALS., INC., Minato-ku, Tokyo (JP)

(72) Inventors: Masaru Kawaguchi, Omuta (JP); Takeshi Nishimura, Yanagawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/871,563

(22) Filed: Sep. 30, 2015

(65) Prior Publication Data

US 2016/0024242 A1    Jan. 28, 2016

Related U.S. Application Data

(63) Continuation of application No. 14/405,222, filed as application No. PCT/JP2013/001207 on Feb. 28, 2013, now Pat. No. 9,181,179.

(30) Foreign Application Priority Data

Aug. 14, 2012  (JP) .................................. 2012-179896

(51) Int. Cl.

| | | |
|---|---|---|
| C08G 18/38 | (2006.01) | |
| C07C 319/20 | (2006.01) | |
| C07C 319/14 | (2006.01) | |
| C07C 335/32 | (2006.01) | |
| C08G 18/76 | (2006.01) | |
| G02B 1/04 | (2006.01) | |
| C07C 319/08 | (2006.01) | |
| C07C 381/00 | (2006.01) | |

(52) U.S. Cl.
CPC ........ *C08G 18/3876* (2013.01); *C07C 319/08* (2013.01); *C07C 319/14* (2013.01); *C07C 319/20* (2013.01); *C07C 335/32* (2013.01); *C07C 381/00* (2013.01); *C08G 18/7642* (2013.01); *G02B 1/041* (2013.01)

(58) Field of Classification Search
None
See application file for complete search history.

(56) References Cited

U.S. PATENT DOCUMENTS

| | | |
|---|---|---|
| 5,087,758 A | 2/1992 | Kanemura et al. |
| 5,191,055 A | 3/1993 | Kanemura et al. |
| 5,608,115 A | 3/1997 | Okazaki et al. |
| 5,837,797 A | 11/1998 | Okazaki et al. |
| 6,100,362 A | 8/2000 | Okazaki et al. |
| 2009/0082544 A1 | 3/2009 | Kuma et al. |
| 2009/0264613 A1 | 10/2009 | Kuma et al. |
| 2010/0280213 A1 | 11/2010 | Kuma et al. |
| 2010/0298521 A1 | 11/2010 | Kuma et al. |
| 2011/0176220 A1 | 7/2011 | Kuma et al. |
| 2011/0178264 A1 | 7/2011 | Kuma et al. |

FOREIGN PATENT DOCUMENTS

| | | |
|---|---|---|
| EP | 0378895 A1 | 7/1990 |
| JP | 2-270859 A | 11/1990 |
| JP | 7-252207 A | 10/1995 |
| JP | 2001-039944 A | 2/2001 |
| KR | 92-005917 B1 | 7/1992 |
| KR | 10-2012-0058635 A | 6/2012 |
| WO | WO 2007/129449 A1 | 11/2007 |
| WO | WO 2007/129450 A1 | 11/2007 |

OTHER PUBLICATIONS

International Search Report (PCT/ISA/210) mailed on May 21, 2013, by the Japanese Patent Office as the International Searching Authority for International Application No. PCT/JP2013/001207.
Office Action issued in corresponding Korean Application No. 2014-7032265 on Apr. 2, 2015 (4 pages).
machine translation of Korean office action for Korean Application No. 10-2014-7032265 on Apr. 2, 2015 (3 pages).

*Primary Examiner* — Rosalynd Keys
(74) *Attorney, Agent, or Firm* — Buchanan, Ingersoll & Rooney PC

(57) ABSTRACT

Provided is a method for producing a molded product comprising a step for preparing a polymerizable composition for optical materials and a step for curing the polymerizable composition for optical materials to produce the molded product. The step for preparing the polymerizable composition for optical materials comprises a step for preparing a defined polythiol compound and a step for preparing the polymerizable composition for optical materials from the polythiol compound. The step for preparing the defined polythiol compound comprises reacting 2-mercaptoethanol with a defined epihalohydrin compound at a temperature of 10° C. to 50° C. to obtain a defined polyalcohol compound, reacting the polyalcohol compound with thiourea in the presence of hydrogen chloride to obtain an isothiuronium salt, hydrolyzing the isothiuronium salt to obtain the polythiol compound, adding hydrochloric acid at a defined concentration to a solution of the polythiol compound, and washing the solution to purify the polythiol compound.

4 Claims, No Drawings

METHOD FOR PRODUCING POLYTHIOL COMPOUND, POLYMERIZABLE COMPOSITION FOR OPTICAL MATERIAL, AND USES THEREOF

TECHNICAL FIELD

The present invention relates to a method for producing a polythiol compound, a polymerizable composition for optical materials, and uses thereof.

BACKGROUND ART

Plastic lenses are lightweight, not easily breakable and tintable as compared with inorganic lenses. Therefore, in recent years, plastic lenses have rapidly been in wide use in optical devices such as spectacle lenses and camera lenses.

It has become necessary for resins for plastic lenses to have more enhanced performances, and there have been demands for an increase in the refractive index, an increase in the Abbe number, a decrease in specific gravity, an increase in heat resistance, and the like. Thus, a variety resin materials for lenses have been hitherto developed and used.

Among others, optical materials formed from polythiourethane-based resins have high refractive index and high Abbe numbers, and are excellent in impact resistance, tintability, processability, and the like. Polythiourethane-based resins are obtained by allowing polythiols to react with polyiso(thio)cyanate compounds and the like.

It is required that in the case of being used in plastic lenses, polythiourethane-based resins be less color, have excellent resin colors, and be transparent. If the quality of polythiol is poor, the quality of the resin thus obtainable may also be poor.

The method for producing a polythiol is exemplified in the following patent documents.

Patent Document 1 or 2 describes a method of obtaining a particular polythiol compound by reacting 2-mercaptoethanol with epichlorohydrin, reacting the compound thus obtained with thiourea to obtain an isothiuronium salt, and then hydrolyzing the isothiuronium salt.

Patent Document 3 describes a method for producing a polythiol compound, the method including adjusting the amount of particular impurities that are contained in 2-mercaptoethanol to a predetermined range.

Patent Document 4 describes a method for producing a polythiol compound, the method including adjusting the content of calcium that is contained in thiourea to a predetermined range.

Patent Document 5 describes a method for producing a polythiol compound, the method including adjusting the content of calcium that is contained in thiourea, and the amount of particular impurities that are contained in 2-mercaptoethanol, to predetermined ranges.

RELATED DOCUMENT

Patent Document

[Patent Document 1] Japanese Unexamined Patent Publication No. 2-270859
[Patent Document 2] Japanese Unexamined Patent Publication No. 7-252207
[Patent Document 3] Pamphlet of International Publication No. WO 2007/129449
[Patent Document 4] Pamphlet of International Publication No. WO 2007/129450
[Patent Document 5] Korean Patent Publication No. 10-2012-0058635

DISCLOSURE OF THE INVENTION

However, in the case where a plastic lens formed from a polythiourethane-based resin is produced using a polythiol compound that is obtainable by the methods described these documents, there is room for an improvement in quality such as color, transparency and striation.

There have been cases, in which even if there is no problem in the product quality when a plastic lens is produced using a polythiol compound obtained by small-scale production, the quality of the polythiol compound fluctuates between different production batches when a polythiol compound is produced continuously and repeatedly in the production in an actual industrial scale. Furthermore, there have been occasions in which when a plastic lens is produced using such a polythiol compound, a plastic lens having a problem in quality such as color, transparency and optical homogeneity is obtained. That is, the efficiency percentage (number of items of quality product/total number of produced items), which includes plastic lenses that satisfy the product quality described above among the plastic lenses obtainable from a polythiol compound, has decreased in some cases.

However, there have been occasions in which defective polythiol compounds occur in large quantities without its cause being understood. Furthermore, there have been an issue that an evaluation of the quality of a polythiol compound as a monomer is difficult, based on the chemical analysis results of the polythiol compound, and judgment must be made based on the evaluation of a plastic lens that can be actually obtained from the polythiol compound. A polythiol compound with which a plastic lens having a desired product quality cannot be obtained in industrial production, cannot be used as a monomer. Therefore, it is very important, in view of the industrial production efficiency of the polythiol compound and in view of economic efficiency, to establish a method for producing a polythiol compound by which a plastic lens product having a desired product quality can be stably obtained.

It is because a plastic lens formed from a thiourethane resin is produced at a rate of one sheet of lens per batch. Specifically, first, a thiourethane-based polymerizable composition is injected into a glass type mold, the polymerizable composition is polymerized under heating to cure, and then the cured product is released from the glass type mold. Thus, one sheet of lens is produced. That is, in order to obtain one sheet of a thiourethane-based plastic lens, many processes and operations are needed. Furthermore, if a thiourethane-based plastic lens is not proved to have a desired product quality, it is difficult to reuse the plastic lens as a thiourethane resin, unlike those products formed from thermoplastic resins and the like. Therefore, it is very important to establish a method for producing a polythiol compound by which a plastic lens product having a desired product quality can be stably obtained, in view of the industrial production efficiency of plastic lenses and in view of economic efficiency.

Therefore, in the case of continuously and repeatedly producing a polythiol compound in an industrial scale, it is necessary to establish a method for producing a polythiol compound with excellent production stability, by which a polythiol compound that is used as a raw material for plastic lenses having a desired product quality is stably obtained without any fluctuation in the product quality of the polythiol compound between different production batches.

The present invention can be described as follows.

[1] A method for producing a polythiol compound, the method comprising:

a step for reacting 2-mercaptoethanol with an epihalohydrin compound represented by the following formula (1)

(1)

wherein X represents a halogen atom, at a temperature of 10° C. to 50° C. to obtain a polyalcohol compound represented by the following formula (2);

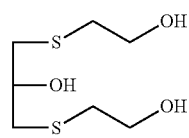
(2)

a step for reacting the polyalcohol compound represented by formula (2) thus obtained with thiourea in the presence of hydrogen chloride to obtain an isothiuronium salt;

a step for adding, while maintaining a reaction solution containing an isothiuronium salt thus obtained at a temperature of 15° C. to 60° C., aqueous ammonia to the reaction solution within 80 minutes to hydrolyze the isothiuronium salt to obtain a polythiol compound represented by the following formula (5);

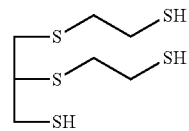
(5)

and a step for adding hydrochloric acid which is a concentration of 25% to 36% to a solution containing the polythiol compound thus obtained, washing the solution at a temperature of 10° C. to 50° C. to purify the polythiol compound.

[2] The method for producing a polythiol compound according to [1], wherein the step for reacting 2-mercaptoethanol with an epihalohydrin compound comprises:

a step for reacting 2-mercaptoethanol with the epihalohydrin compound represented by formula (1) at a temperature of 10° C. to 20° C. to obtain a compound represented by the following formula (3);

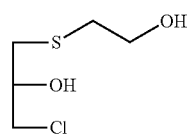
(3)

and a step for reacting the compound represented by formula (3) with 2-mercaptoethanol at a temperature of 10° C. to 50° C. to obtain the polyalcohol compound represented by formula (2).

[3] A method for industrial manufacture of a polythiol compound, using the method according to [1] or [2].

[4] A polymerizable composition for optical materials, comprising a polythiol compound obtained by the method according to any one of [1] to [3].

[5] A molded product obtained by curing the polymerizable composition for optical materials according to [4].

[6] A plastic lens comprising the molded product according to [5].

In addition, washing according to the invention means a process of stirring and mixing an organic layer containing a product in water or an aqueous acid or alkali solution, causing the mixture to stand still, subsequently separating the mixture to liquid-liquid partition, and thus obtaining an organic layer containing a reaction product. Water washing means washing using water, acid washing means washing using an acidic aqueous solution, and alkali (aqueous ammonia) washing means washing using an aqueous alkali solution (aqueous ammonia).

When a polythiol compound that is obtainable from the method for producing a polythiol compound of the invention is used, a plastic lens formed from a polythiourethane-based resin having excellent quality such as color, transparency and striation can be obtained.

Furthermore, according to the invention, even in the case where a polythiol compound is produced repeatedly in actual production on an industrial scale, no fluctuation occurs in the product quality of the polythiol compound between different production batches, a plastic lens having a desired product quality can be stably obtained, and a production method for a polythiol compound with excellent production stability can be provided. Furthermore, a polythiol compound which is suitable as a raw material for plastic lenses can be stably supplied. Furthermore, when a polythiol compound obtained by such a method is used, the product yield and the efficiency percentage of the product thus obtainable can be improved.

DESCRIPTION OF EMBODIMENTS

The "method for producing polythiol compounds including 4-mercaptomethyl-1,8-dimercapto-3,6-dithiaoctane as a main component (hereinafter, simply a polythiol compound)" of the invention will be described based on the following exemplary embodiment.

The method for producing a polythiol compound of the present exemplary embodiment can include the steps described below.

Step A: 2-mercaptoethanol is reacted with an epihalohydrin compound represented by the following formula (1) at a temperature of 10° C. to 50° C., and thus a polyalcohol compound represented by the following formula (2) is obtained.

(1)

(wherein X represents a halogen atom)

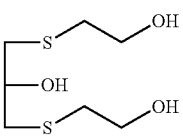
(2)

Step B: The polyalcohol compound obtained in step A is reacted with thiourea in the presence of hydrogen chloride, and thus an isothiuronium salt is obtained.

Step C: While a reaction solution containing the isothiuronium salt obtained in step B is maintained at a temperature of 15° C. to 60° C., aqueous ammonia is added to the reaction solution within 80 minutes, the isothiuronium salt is hydrolyzed, and thus a polythiol compound represented by the following formula (5) is obtained.

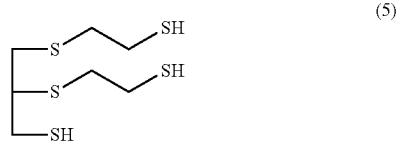
(5)

Step D: Hydrochloric acid which is a concentration of 25% to 36% is added to the solution containing the polythiol compound obtained in step C, the solution is washed at a temperature of 10° C. to 50° C., and the polythiol compound is purified.

According to the production method of the present exemplary embodiment, a plastic lens formed from a polythiourethane-based resin produced using a polythiol compound that is obtained by performing step A, step C and step D in particular within the scope of the invention, has excellent quality such as color, transparency and striation. Furthermore, according to the production method of the present exemplary embodiment, even in the case where a polythiol compound is repeatedly produced in actual production on an industrial scale, a polythiol compound having a desired product quality can be stably obtained without any fluctuation in the product quality of the polythiol compound between different production batches, and the production stability is excellent. The production method of the present exemplary embodiment is particularly useful as a method for industrial manufacture of a polythiol compound.

Hereinafter, the various processes will be described in sequence.

(Step A)

In step A, 2-mercaptoethanol is reacted with an epihalohydrin compound represented by the following formula (1), and thereby a triol compound represented by the following formula (2) can be obtained as a polyalcohol compound.

(1)

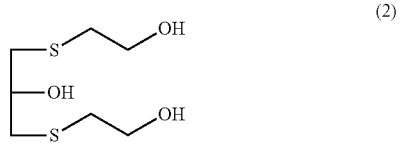
(2)

In the formula (1), X represents a halogen atom which may be a fluorine atom, a chlorine atom, a bromine atom or an iodine atom, and is preferably a chlorine atom.

In the present exemplary embodiment, the reaction can be carried out at a temperature in the range of 10° C. to 50° C., preferably 15° C. to 50° C., and more preferably 25° C. to 45° C. When the reaction temperature is lower than 10° C., the reaction does not sufficiently proceed throughout the reaction process, and unreacted elements may be retained in the reaction system, causing the reaction to proceed suddenly. When the reaction temperature is higher than 50° C., the color of the lens may be deteriorated. That is, when the reaction temperature is in the temperature range described above, excellent controllability of the reaction is attained, and the color of the plastic lens thus obtainable is also excellent.

The reaction can be carried out for 2 hours to 12 hours, and preferably 3 hours to 10 hours.

The reaction can be carried out, for example, in the following manner. First, 2-mercaptoethanol and a base are added, if necessary, to water or a lower alcohol solvent such as methanol or ethanol, subsequently an epihalohydrin is added dropwise thereto, and thus a reaction is carried out. The reaction temperature and the reaction time are preferably adjusted to be in the ranges described above. The reaction time includes the time for the dropwise addition of the epihalohydrin, and the temperature of the reaction solution at the time of the dropwise addition needs to be adjusted to the reaction temperature. The use amount of 2-mercaptoethanol is necessarily equal to or more than 1.8 moles and equal to or less than 3 moles relative to 1 mole of the epihalohydrin, and the use amount is preferably equal to or more than 1.8 moles and equal to or less than 3 moles, and more preferably equal to or more than 1.9 moles and equal to or less than 2.1 moles, relative to 1 mole of the epihalohydrin.

Examples of the base include metal hydroxides such as sodium hydroxide and potassium hydroxide; metal carbonates such as sodium carbonate and potassium carbonate; and tertiary amines such as triethylamine and tributylamine. However, from the viewpoints of reactivity and economic efficiency, sodium hydroxide is most preferred. The use amount of the base is, in the case of a monovalent base, equal to or more than 0.5 moles and equal to or less than 2 moles, and preferably equal to or more than 0.9 moles and equal to or less than 1.1 moles, relative to 1 mole of the epihalohydrin. In the case of a divalent base, the use amount of the base is preferably an amount equivalent to a half the use amount of the monovalent base. The base can be used as an aqueous solution, an alcohol solution or the like, and when the base is used as a solution, the concentration of the base can be appropriately selected.

Furthermore, in addition to the method described above, a triol compound represented by formula (2) can also be obtained by a two-steps reaction of first producing a diol compound represented by the following formula (3), and then adding 2-mercaptoethanol dropwise thereto.

In this method, first, 2-mercaptoethanol is reacted with the epihalohydrin compound represented by formula (1) described above, and thus a compound represented by the following formula (3) is obtained.

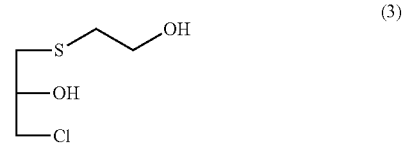
(3)

The reaction temperature is 10° C. to 20° C. The reaction time is about 2 hours to 10 hours.

Subsequently, the compound represented by formula (3) is reacted with 2-mercaptoethanol, and thus a triol compound represented by formula (2) is obtained. The reaction temperature is 10° C. to 50° C., preferably 15° C. to 50° C., and more preferably 25° C. to 45° C. The reaction time is about 2 hours to 12 hours.

When these processes are carried out in the temperature ranges described above, excellent controllability of the reaction is attained, and the color of the plastic lens thus obtainable is also excellent.

The method can be carried out specifically in the following manner.

First, an epihalohydrin is added dropwise into 2-mercaptoethanol and if necessary, water, or a lower alcohol such as methanol or ethanol and a catalytic amount of a base in an aqueous solution or lower alcohol solution of methanol or ethanol. The reaction temperature and the reaction time are preferably adjusted to be in the ranges described above. The use amount of 2-mercaptoethanol in the solution to which the epihalohydrin is added dropwise is equal to or more than 1 mole and equal to or less than 3 moles, and preferably equal to or more than 1 mole and equal to or less than 2 moles, relative to 1 mole of the epihalohydrin. Furthermore, a catalytic amount of the base is used, and the use amount of the base is, in the case of a monovalent base, equal to or more than 0.001 moles and equal to or less than 0.1 moles with respect to the epihalohydrin. In the case of a divalent base, the use amount is preferably an amount equivalent to a half the use amount of the monovalent base. The base can be used as an aqueous solution, an alcohol solution or the like, and when the base is used as a solution, the concentration of the base can be appropriately selected. As an epihalohydrin is added dropwise to the solution, a diol compound represented by formula (3) is obtained.

Subsequently, the epihalohydrin is added such that the amount of 2-mercaptoethanol is equal to or more than 1.5 moles and equal to or less than 3.0 moles relative to 1 mole of the epihalohydrin, and if there is a deficit, 2-mercaptoethanol is further added, and a deficit of the base is added to the epihalohydrin such that the amount of the base is equal to or more than 1.0 mole and equal to or less than 2.0 moles. Thus, a polyalcohol compound represented by formula (2) can be obtained. The reaction temperature and the reaction time are preferably adjusted to the ranges described above.

In regard to the synthesis of the diol compound represented by formula (3), the reaction temperature in the case of using a strong base such as sodium hydroxide is appropriately adjusted to equal to or higher than 10° C. and equal to or lower than 50° C. If the reaction temperature is too high, the base added in a catalytic amount is consumed in a reaction which produces a polyalcohol compound from the diol compound, and there is a possibility that the yield of the diol form may decrease.

(Step B)

Next, the polyalcohol compound represented by formula (2) that has been obtained in step A is reacted with thiourea in the presence of hydrogen chloride, and thus an isothiuronium salt is obtained.

Specifically, thiourea is added to the polyalcohol compound represented by formula (2) in an amount of 2.7 moles or more, preferably equal to or more than 2.7 moles and equal to or less than 6.0 moles, and more preferably equal to or more than 2.9 moles and equal to or less than 3.2 moles, relative to 1 mole of the polyalcohol compound, and thus the components are reacted with each other. The reaction is carried out in the presence of hydrogen chloride in an amount of 3 moles or more, preferably equal to or more than 3 moles and equal to or less than 12 moles, and more preferably equal to or more than 3 moles and equal to or less than 5 moles, relative to 1 mole of the polyalcohol compound, at a temperature in the range of from room temperature to the reflux temperature, and preferably 90° C. to 120° C., for about 1 hour to 10 hours. An isothiuronium salt compound is formed by the reaction between a polyalcohol compound and thiourea. When hydrogen chloride is used, a sufficient rate of reaction is obtained, and also, coloration of the thiol compound and the color of the plastic lens thus obtainable can be controlled. Regarding the hydrogen chloride, an aqueous solution of hydrochloric acid or hydrogen chloride gas can be used. When an aqueous solution of hydrochloric acid is used, the concentration can be appropriately selected.

(Step C)

Aqueous ammonia is added to a reaction solution containing the isothiuronium salt obtained in step B, and the isothiuronium salt is hydrolyzed. Thus, a polythiol compound is obtained. As the polythiol compound, a polythiol compound containing 4-mercaptomethyl-1,8-dimercapto-3,6-dithiaoctane represented by the following formula (5) as a main component can be obtained.

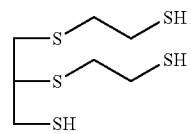

(5)

Specifically, while a reaction solution containing the isothiuronium salt is maintained at a temperature in the range of 15° C. to 60° C., preferably 31° C. to 55° C., and more preferably 31° C. to 45° C., aqueous ammonia is added to the reaction solution for 80 minutes or less, preferably 70 minutes or less, and more preferably 20 minutes to 60 minutes. It is preferable if the time for which aqueous ammonia is added is shorter, but in view of the capacity of the facilities such as the cooling capacity, the time is set to the range of the time period described above.

When a hydrolytic reaction is carried out under such conditions, plastic lenses having a desired product quality can be stably obtained in continuous production on an industrial scale. That is, when this polythiol compound is used, plastic lenses formed from a polythiourethane-based resin having excellent quality such as color, transparency and striation can be obtained with a stabilized product quality. That is, the product yield or the efficiency percentage of the product can be improved by the hydrolytic reaction of the present exemplary embodiment.

It is preferable to add an organic solvent before aqueous ammonia is added. When an organic solvent is added, the product quality such as color of the plastic lenses thus obtainable is improved. The amount of the organic solvent added is appropriately selected depending on the kind of the solvent or the like, but the organic solvent can be added in an amount of 0.1 to 3.0 times, and preferably 0.2 to 1.0 times the amount of the thiuronium salt reaction solution. Examples of the organic solvent include toluene, xylene, chlorobenzene, and dichlorobenzene. From the viewpoint of the effects described above, toluene is preferred.

Aqueous ammonia can be added in an amount of, in terms of ammonia ($NH_3$), 1 mole or more, preferably equal to or more than 1 mole and equal to or less than 3 moles, and more preferably equal to or more than 1.1 moles and equal to or less than 2 moles, relative to 1 mole of the use amount of hydrogen chloride described above, within the addition time described above. The concentration of aqueous ammonia can be adjusted to 10% to 25%. Furthermore, ammonia gas can also be used instead of aqueous ammonia. In the case of adding ammonia gas in substitution of the entirety or a portion of aqueous ammonia, the reaction can be carried out under the same conditions (use amount, addition time, and addition temperature) as those in a case where aqueous ammonia is used.

In the present exemplary embodiment, ammonia ($NH_3$) is added at a rate of addition of 1.25 mol %/min or more, preferably equal to or more than 1.25 mol %/min and equal to or less than 3.75 mol %/min, and more preferably equal to or more than 1.38 mol %/min and equal to or less than 2.5 mol %/min, relative to 1 mole of hydrogen chloride. In the present process, it is not necessary to add ammonia continuously at the above-described rate, and it is acceptable if the average rate of addition of the addition time described above is included in this range.

After aqueous ammonia is added, the hydrolytic reaction is carried out continuously at a temperature in the range of from room temperature to the reflux temperature, and preferably 30° C. to 80° C., for about 1 hour to 8 hours.

(Step D)

In the present exemplary embodiment, the polythiol compound obtained in step C is purified by washing.

Specifically, acid washing and then several times of water washing can be carried out. Water washing can also be carried out before acid washing, and alkali washing can also be carried out after acid washing. The number of water washing can be reduced by alkali washing. Impurities and the like can be efficiently removed by the washing process. When purification by such washing is performed, the color of the plastic lenses obtained from the polythiol compound is improved, and high quality plastic lenses with reduced occurrence of clouding and striation can be produced with a high yield, while the efficiency percentage is also improved. Examples of preferred embodiments include a method of performing water washing-acid washing-water washing-alkali washing-water washing after hydrolysis; a method of performing acid washing-water washing-alkali washing-water washing; and a method of performing acid washing-water washing. The respective washing processes may be repeated several times.

Acid washing can be carried out by adding hydrochloric acid to the solution containing the polythiol compound thus obtained. The concentration of hydrochloric acid can be adjusted to 25% to 36%, and preferably 30% to 36%. When the concentration of hydrochloric acid is lower than 25%, clouding may occur in the plastic lens due to impurities and the like. Furthermore, the temperature of acid washing can be set to 10° C. to 50° C., preferably 15° C. to 50° C., more preferably 20° C. to 50° C., and even more preferably 30° C. to 45° C.

When the concentration of hydrochloric acid and the temperature conditions are satisfied, plastic lenses having excellent color and reduced clouding can be obtained with a high product yield, and the efficiency percentage is also improved.

Water washing can be achieved by using degassed water having an oxygen concentration of 5 mg/L or less.

Examples of the method for producing degassed water include a method of purging dissolved oxygen by bubbling nitrogen; a method of purging dissolved oxygen by a heating treatment; and a method of purging dissolved oxygen by vacuum degassing. However, there are no particular limitations on the method as long as the oxygen concentration can be adjusted to 5 mg/L or less.

Thereby, color or clouding that causes a problem in optical materials such as plastic lenses can be effectively suppressed.

Furthermore, alkali washing can be carried out by adding an alkaline aqueous solution, and stirring the mixture at a temperature in the range of 20° C. to 50° C. for 10 minutes to 3 hours. The alkaline aqueous solution is preferably aqueous ammonia. Furthermore, the concentration of aqueous ammonia can be set to 0.1% to 10%, preferably 0.1% to 1%, and more preferably 0.1% to 0.5%.

Also for acid washing and alkali washing, when water having an oxygen concentration of 5 mg/L or less is used, color or clouding that causes a problem in optical materials such as plastic lenses can be effectively suppressed.

After step D, a solvent removal process, and if necessary, a low boiling point-compound removal process, a filtering process, and a distillation process are carried out, and thus a polythiol compound containing 4-mercaptomethyl-1,8-dimercapto-3,6-dithiaoctane can be obtained as a polythiol compound.

The solvent removal process is a process of removing the organic solvent at normal pressure or under reduced pressure. The degree of pressure reduction and the temperature may be appropriately selected depending on the solvent used or the like, however it is preferable to carry out the solvent removal process under reduced pressure and at 100° C. or lower, and preferably 85° C. or lower.

The low boiling point compound removal process is a process of removing any included low boiling point compounds at normal pressure or under reduced pressure, after the solvent removal process. The degree of pressure reduction and the temperature may be appropriately selected depending on the solvent used or the like, however it is preferable to carry out the low boiling point compound removal process under reduced pressure and at 100° C. or lower, and preferably 85° C. or lower. At that time, the process may also be carried out while an inert gas such as nitrogen gas is blown in.

The filtering process is a process of removing solids such as salts by filtration. The method for filtration or the like is appropriately selected, for example filtration under reduced pressure or filtration under added pressure using a membrane filter or a cartridge filter can be used. It is preferable to carry out the process using a filter having a pore size of 5 μm or less, and preferably 2 μm or less.

The distillation process is a process of purifying the polythiol compound by distillation. The degree of pressure reduction and the temperature may be appropriately selected depending on the solvent used or the like, however it is preferable to carry out the distillation process under reduced pressure and at 250° C. or lower, and preferably 200° C. or lower.

In addition, the production process of the present exemplary embodiment can be carried out in air, but it is preferable to carry out the entire process in a nitrogen atmosphere, from the viewpoint of color.

<Polymerizable Composition for Optical Materials>

The polymerizable composition for optical materials according to the present exemplary embodiment includes a polythiol compound for optical materials obtained by the method described above, and a polyiso(thio)cyanate compound.

The polyiso(thio)cyanate compound is not particularly limited as long as it is a compound having at least two or more iso(thio)cyanate groups in one molecule, and specific examples include aliphatic polyisocyanate compounds such as hexamethylene diisocyanate, 1,5-pentane diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl) carbonate, bis(isocyanatoethyl) ether, lysine diisocyanate methyl ester, and lysine triisocyanate;

alicyclic polyisocyanate compounds such as isophorone diisocyanate, bis(isocyanatomethyl)cyclohexane, dicyclohexylmethane diisocyanate, cyclohexane diisocyanate, methylcyclohexane diisocyanate, dicyclohexyl dimethylmethane isocyanate, 2,5-bis(isocyanatomethyl)-bicyclo[2.2.1]heptane, 2,6-bis(isocyanatomethyl)-bicyclo[2.2.1]heptane, 3,8-bis(isocyanatomethyl)tricyclodecane, 3,9-bis(isocyanatomethyl)tricyclodecane, 4,8-bis(isocyanatomethyl)tricyclodecane, 4,9-bis(isocyanatomethyl)tricyclodecane, bis(4-isocyanatocyclohexyl)methane, 1,3-bis(isocyanatomethyl)cyclohexane, and 1,4-bis(isocyanatomethyl)cyclohexane;

polyisocyanate compounds having aromatic ring compounds, such as 1,2-diisocyanatobenzene, 1,3-diisocyanatobenzene, 1,4-diisocyanatobenzene, tolylene diisocyanate, 2,4-diisocyanatotoluene, 2,6-diisocyanatotoluene, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4'-methylenebis(phenyl isocyanate), 4,4'-methylenebis(2-methylphenyl isocyanate), bibenzyl-4,4'-diisocyanate, bis(isocyanatophenyl)ethylene, bis(isocyanatomethyl)benzene, m-xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethylphenyl) ether, bis(isocyanatoethyl) phthalate, and 2,5-di(isocyanatomethyl)furan;

sulfur-containing aliphatic polyisocyanate compounds such as bis(isocyanatomethyl) sulfide, bis(isocyanatoethyl) sulfide, bis(isocyanatopropyl) sulfide, bis(isocyanatohexyl) sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatomethylthio)ethane, bis(isocyanatoethylthio)ethane, 1,5-diisocyanato-2-isocyanatomethyl-3-thiapentane, 1,2,3-tris(isocyanatomethylthio)propane, 1,2,3-tris(isocyanatoethylthio)propane, 3,5-dithia-1,2,6,7-heptane tetraisocyanate, 2,6-diisocyanatomethyl-3,5-dithia-1,7-heptane diisocyanate, 2,5-diisocyanatomethylthiophene, and 4-isocyanatoethylthio-2,6-dithia-1,8-octane diisocyanate;

aromatic sulfide-based polyisocyanate compounds such as 2-isocyanatophenyl-4-isocyanatophenyl sulfide, bis(4-isocyanatophenyl) sulfide, bis(4-isocyanatomethylphenyl) sulfide;

aromatic disulfide-based polyisocyanate compounds such as bis(4-isocyanatophenyl)disulfide, bis(2-methyl-5-isocyanatophenyl)disulfide, bis(3-methyl-5-isocyanatophenyl)disulfide, bis(3-methyl-6-isocyanatophenyl)disulfide, bis(4-methyl-5-isocyanatophenyl)disulfide, and bis(4-methoxy-3-isocyanatophenyl)disulfide;

sulfur-containing alicyclic polyisocyanate compounds such as 2,5-diisocyanatotetrahydrothiophene, 2,5-diisocyanatomethyltetrahydrothiophene, 3,4-diisocyanatomethyltetrahydrothiophene, 2,5-diisocyanto-1,4-dithiane, 2,5-diisocyantomethyl-1,4-dithiane, 4,5-diisocynato-1,3-dithiolane, 4,5-bis(isocyantomethyl)-1,3-dithiolane, and 4,5-diisocyantomethyl-2-methyl-1,3-dithiolane;

aliphatic polyisothiocyanate compounds such as 1,2-diisothiocyanatoethane and 1,6-diisothiocyanatohexane; alicyclic polyisothiocyanate compounds such as cyclohexane diisothiocyanate; aromatic polyisothiocyanate compounds such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-methylenebis(phenyl isothiocyanate), 4,4'-methylenebis(2-methylphenyl isothiocyanate), 4,4'-methylenebis(3-methylphenyl isothiocyanate), 4,4'-diisothiocyanatobenzophenone, 4,4'-diisothiocyanato-3,3'-dimethylbenzophenone, and bis(4-isothiocyanatophenyl) ether;

carbonyl polyisothiocyanate compounds such as 1,3-benzene dicarbonyl diisothiocyanate, 1,4-benzene dicarbonyl diisothiocyanate, and (2,2-pyridine)-4,4-dicarbonyl diisothiocyanate; sulfur-containing aliphatic polyisothiocyanate compounds such as thiobis(3-isothiocyanatopropane), thiobis(2-isothiocyanatoethane), and dithiobis(2-isothiocyanatoethane);

sulfur-containing aromatic polyisothiocyanate compounds such as 1-isothiocyanato-4-[(2-isothiocyanato)sulfonyl]benzene, thiobis(4-isothiocyanatobenzene), sulfonyl(4-isothiocyanatobenzene), and dithiobis(4-isothiocyanatobenzene); sulfur-containing alicyclic polyisothiocyanate compounds such as 2,5-diisothiocyanatothiophene and 2,5-diisothiocyanato-1,4-dithiane; and compounds having isocyanato groups and isothiocyanato groups, such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanato-1,3,5-triazine, 4-isocyanatophenyl-4-isothiocyanatophenyl sulfide, and 2-isocyanatoethyl-2-isothiocyanatoethyl disulfide.

Preferred examples of the polyiso (thio) cyanate compound include aliphatic polyisocyanate compounds such as hexamethylene diisocyanate, 1,5-pentane diisocyanate, isophorone diisocyanate, bis(isocyanatomethyl)cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl)methane, 1,3-bis(isocyanatomethyl)cyclohexane, and 1,4-bis(isocyanatomethyl)cyclohexane; and polyisocyanate compounds having aromatic ring compounds, such as bis(isocyanatomethyl)benzene, m-xylylene diisocyanate, 1,3-diisocyanatobenzene, tolylene diisocyanate, 2,4-diisocyanatotoluene, 2,6-diisocyanatotoluene, 4,4'-methylenebis(phenyl isocyanate).

Furthermore, halogen-substituted forms such as chlorine-substituted forms and bromine-substituted forms, alkyl-substituted forms, alkoxy-substituted forms, nitro-substituted forms, prepolymer type modified forms associated with polyhydric alcohols, carbodiimide-modified forms, urea-modified forms, biuret-modified forms, dimerized or trimerized reaction products and the like of those compounds described above can also be used. These compounds may be used alone, or mixtures of two or more kinds may be used.

Regarding the polythiol compound used in the polymerizable composition for optical materials, other polythiol compounds for optical materials can also be used in addition to the polythiol compounds for optical materials obtained by the method described above.

Preferred examples of the other polythiol compounds for optical materials include aliphatic polythiol compounds such as methanedithiol, 1,2-ethanedithiol, 1,2,3-propanetrithiol, pentaerythritol tetrakis(2-mercaptoacetate), pentaerythritol tetrakis(3-mercaptopropionate), bis(mercaptoethyl) sulfide, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 2,5-dimercaptomethyl-1,4-dithiane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl) sulfide, 2,5-dimercaptomethyl-1,4-dithiane, 2,5-dimercapto-1,4-dithiane, 2,5-dimercaptomethyl-2,5-dimethyl-1,4-dithiane, 1,1,3,3-tetrakis(mercaptomethylthio)propane, 1,1,2,2-tetrakis(mercaptomethylthio)ethane, and 4,6-bis(mercaptomethylthio)-1,3-dithiane.

The use ratio of the polythiol compound and the polyiso(thio)cyanate compound is not particularly limited, however usually, the molar ratio of SH group/NCO group is in the range of 0.5 to 3.0, preferably in the range of 0.6 to 2.0, and more preferably in the range of 0.8 to 1.3. When the use ratio is in the range described above, various performances such as the refractive index and heat resistance that are required in optical materials such as plastic lenses and transparent materials can be satisfied in a well-balanced manner.

For the purpose of improving various properties, operability and polymerization reactivity of the polythiourethane-based resin of the invention, other substances may be added in addition to the polythiol compound and iso(thio)cyanate compound that form the urethane resin. For example, in addition to the urethane-forming raw materials, one kind or two or more kinds of active hydrogen compounds represented by amine or the like, carbonate compounds, ester compounds, metals, metal oxides, organometallic compounds, and inorganic substances may also be added.

Furthermore, various substances such as a chain extending agent, a crosslinking agent, a photostabilizer, an ultraviolet absorber, an oxidation inhibitor, an oil-soluble dye, a filler, and a mold releasing agent may also be added according to the purpose, similarly to known molding methods. In order to adjust the rate of reaction to a desired value, thiocarbamic acid S-alkyl ester, or a known reaction catalyst that is used in the production of polythiourethane-based resins may also be appropriately added.

Regarding the reaction catalyst, thiocarbamic acid S-alkyl ester, or a known reaction catalyst that is used in the production of polythiourethane-based resins can be appropriately added.

Examples of the reaction catalyst include dialkyltin halides such as dibutyltin dichloride and dimethyltin dichloride; dialkyltin dicarboxylates such as dimethyltin diacetate, dibutyltin dioctanoate, and dibutyltin dilaurate; dialkyltin dialkoxides such as dibutyltin dibutoxide and dioctyltin dibutoxide; dialkyltin dithioalkoxides such as dibutyltin di(thiobutoxide); dialkyltin oxides such as di(2-ethylhexyl) tin oxide, dioctyltin oxide, and bis(butoxydibutyltin) oxide; and dialkyltin sulfides such as dibutyltin sulfide. Suitable examples include dialkyltin halides such as dibutyltin dichloride and dimethyltin dichloride.

Furthermore, for the purpose of modifying the resin, resin modifying agents such as a hydroxyl compound, an epoxy compound, an episulfide compound, an organic acid and an anhydride thereof, and an olefin compound containing a (meth)acrylate compound or the like may also be added. Here, the resin modifying agent is a compound which regulates or enhances properties such as refractive index, Abbe number, heat resistance and specific gravity, and mechanical strength such as impact resistance of a material formed from a thiourethane-based resin.

Furthermore, the polymerizable composition for optical materials of the present exemplary embodiment may include a bluing agent as necessary. The bluing agent has an absorption band in the wavelength range of from orange color to yellow color in the visible light region, and has a function of regulating the color of an optical material formed from a resin. More specifically, the bluing agent contains a substance which displays from blue color to violet color.

There are no particular limitations on the bluing agent that is used in the polymerizable composition for optical materials of the present exemplary embodiment, and specific examples include dyes, fluorescent brightening agents, fluorescent pigments, and inorganic pigments. The bluing agent is appropriately selected among those that can be used as bluing agents, in accordance with the properties required from optical components, resin color, and the like. These bluing agents may be used respectively alone, or two or more kinds may be used in combination.

Among these bluing agents, from the viewpoint of solubility in the polymerizable composition and the viewpoint of transparency of the optical material thus obtainable, a dye is preferred.

From the viewpoint of the absorption wavelength, the bluing agent is preferably a dye having a maximum absorption wavelength of equal to or more than 520 nm and equal to or less than 600 nm, and more preferably a dye having a maximum absorption wavelength of equal to or more than 540 nm and equal to or less than 580 nm.

Furthermore, from the viewpoint of the structure of the compound, an anthraquinone-based dye is preferred.

There are no particular limitations on the method for adding the bluing agent, and it is preferable to have the bluing agent added in advance to the monomer system. Regarding the method, various methods such as a method of dissolving the bluing agent in the monomer, and a method of preparing a master solution containing a high concentration of the bluing agent, and adding the bluing agent by diluting the master solution with the monomer used or another additive, can be employed.

Specifically, the polymerizable composition for optical materials of the present exemplary embodiment is obtained as a mixed solution, by mixing the polythiol compound obtained by the production method described above and a polyiso(thio)cyanate compound, with other components as necessary. This mixed solution is subjected to defoaming by an appropriate method according to necessity, subsequently injected the mixed solution into a mold, and polymerized by slowly heating usually from a low temperature to a high temperature.

A molded product formed from the polythiourethane-based resin obtainable by curing the polymerizable composition of the present exemplary embodiment in this manner has features such as a high refractive index, low dispersibility, excellent heat resistance and durability, light weight, and excellent impact resistance. Also, the molded product has satisfactory color, and is suitable as a raw material for optical materials such as spectacle lenses and camera lenses, and transparent materials.

Furthermore, a plastic lens obtained by using the polythiourethane-based resin of the present exemplary embodiment may also be subjected to physical and chemical treatments such as surface polishing, antistatic treatment, hard coating treatment, non-reflective coating treatment, staining treatment, and dimming treatment, in order to perform improvements such as prevention of reflection, impartation of high hardness, enhancement of abrasion resistance, enhancement of chemical resistance, impartation of anti-fogging, and impartation of fashionability.

EXAMPLES

Hereinafter, the present invention will be described in more detail based on Examples, however the invention is not intended to be limited to these.

In the following Examples, properties were measured by the following measurement methods.

APHA: This is a method for indicating the color, and the color was determined using standard liquids prepared by dissolving reagents of platinum and cobalt, and determining a standard liquid dilution having a color density equivalent to that of the color of the sample by making a comparison. Thus, the "degree" of the color was defined as the measured value.

Water content: A sample was dissolved in toluene, and water measurement was carried out using a Karl-Fischer Water Titrate.

Viscosity: The viscosity was measured according to JIS K7117.

Refractive index: The refractive index was measured at 20° C. using a digital refractometer, RA-600, manufactured by Kyoto Electronics Manufacturing Co., Ltd.

Ammonium content: The sample was dissolved in chloroform and extracted with water, and the ammonium content was measured by ion chromatography.

Acid content: The sample was dissolved in a solvent, the solvent was titrated using a methanol solution of KOH, and the acid content was calculated as a HCl content.

Loss degree of transparency of resin: A 9-mm plate was produced under the conditions for the plastic lens production of the Examples, and the loss degree of transparency was measured using a loss degree of transparency analyzer (manufactured by Hayashi Co., Ltd.; LUMINAR ACE LA-150SE).

Resin YI: This is a yellow index for color evaluation, and is measured with a colorimeter. A 9-mm plate was produced under the conditions for the plastic lens production of the Examples, and the YI value was measured using a colorimeter (CR-400) manufactured by Konica Minolta, Inc.

Striation: A lens was produced under the conditions for the plastic lens production of the Examples, and the lens was visually observed under a high pressure mercury lamp. A sample in which no striped pattern was observed was rated as O, and a sample in which a striped pattern was observed was rated as X.

Furthermore, degassed water at a dissolved oxygen concentration of 2 ppm was obtained by bubbling nitrogen into water and thereby purging dissolved oxygen.

Example A-1

Synthesis of Polythiol Compound Containing 4-mercaptomethyl-1,8-dimercapto-3,6-dithiaoctane as Main Component In a reactor, 124.6 parts by weight of 2-mercaptoethanol and 18.3 parts by weight of degassed water (dissolved oxygen concentration: 2 ppm) were introduced. 101.5 parts by weight of a 32 wt % aqueous solution of sodium hydroxide was added dropwise thereto over 40 minutes at 12° C. to 35° C., and then 73.6 parts by weight of epichlorohydrin was added dropwise thereto over 4.5 hours at 29° C. to 36° C. Subsequently, the mixture was stirred for 40 minutes. Production of 1,3-bis(2-hydroxyethylthio)-2-propanol was confirmed from NMR data.

331.5 parts by weight of 35.5% hydrochloric acid was introduced, and then 183.8 parts by weight of thiourea having a purity of 99.90% was introduced. The mixture was stirred for 3 hours under reflux at 110° C., and thereby a reaction which forms thiuronium salt was carried out. The reaction mixture was cooled to 45° C., and then 320.5 parts by weight of toluene was added thereto, and the mixture was cooled to 31° C. 243.1 parts by weight of a 25 wt % aqueous ammonia solution was introduced over 44 minutes at 31° C. to 41° C., and a hydrolytic reaction was carried out by stirring the mixture for 3 hours at 54° C. to 62° C. Thus, a toluene solution of a polythiol containing 4-mercaptomethyl-1,8-dimercapto-3,6-dithiaoctane as a main component was obtained. 162.8 parts by weight of 35.5% hydrochloric acid was added to the toluene solution, and thus the toluene solution was acid washed for 1 hour at 35° C. to 43° C. 174.1 parts by weight of degassed water (dissolved oxygen concentration: 2 ppm) was added, and washing for 30 minutes at 35° C. to 45° C. was carried out two times. 162.1 parts by weight of 0.1% aqueous ammonia was added thereto, and the mixture was washed for 30 minutes. 174.2 parts by weight of degassed water (dissolved oxygen concentration: 2 ppm) was added thereto, and washing for 30 minutes at 35° C. to 45° C. was carried out two times. Toluene and a trace amount of water were removed under heating at reduced pressure, and then the residue was filtered under reduced pressure using a 1.2 μm PTFE type membrane filter, and thus 205.0 parts by weight of a polythiol compound containing 4-mercaptomethyl-1,8-dimercapto-3,6-dithiaoctane as a main component was obtained. The properties of the polythiol compound thus obtained are shown in Table-1.

(Measurement of Viscosity of Polymerizable Composition)

52 parts by weight of m-xylylene diisocyanate, 0.015 parts by weight of dibutyltin dichloride as a curing catalyst, 0.10 parts by weight of ZELEC UN (trade name, product of Stepan Company; acidic phosphoric acid ester), and 0.05 parts by weight of BIOSORB 583 (manufactured by Kyodo chemical Co., Ltd.; ultraviolet absorbent) were mixed and dissolved at 20° C. 48 parts by weight of the polythiol compound containing 4-mercaptomethyl-1,8-dimercapto-3,6-dithiaoctane as a main component thus obtained was introduced and mixed, and thus a mixed uniform solution was obtained. The time of preparation of the mixed uniform solution was defined as 0 hour, and the viscosity after 7 hours was measured with a B type viscometer. The viscosity after 7 hours of the polymerizable composition was used as an index of the rate of polymerization. An evaluation was conducted such that a sample having a viscosity value of 250 mPa·s or less was rated as O, and a sample having a viscosity value of 1000 mPa·s or more was rated as X. The results are shown in Table-2.

The results of an elemental analysis and an NMR analysis of 4-mercaptomethyl-1,8-dimercapto-3,6-dithiaoctane will be shown.

Elemental analysis (as $C_7H_{16}S_5$)

CHS analysis values: 32.12 6.19 61.69 Calculated values: 32.27 6.19 61.53 $^1$H NMR (CDCl$_3$)

$\delta_{ppm}$=1.74 to 1.91 (3H, m, SH)

2.70 to 3.00 (13H, m, CH)

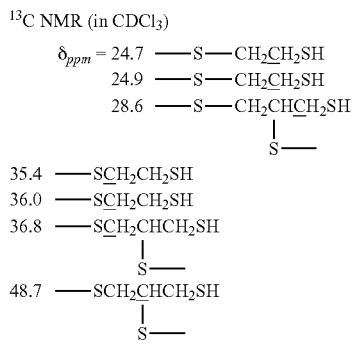

$^{13}$C NMR (in CDCl$_3$)

$\delta_{ppm}$ = 24.7 —S—CH$_2$$\underline{C}$H$_2$SH
24.9 —S—CH$_2$$\underline{C}$H$_2$SH
28.6 —S—CH$_2$$\underline{C}$HCH$_2$SH
           |
           S—
35.4 —S$\underline{C}$H$_2$CH$_2$SH
36.0 —S$\underline{C}$H$_2$CH$_2$SH
36.8 —S$\underline{C}$H$_2$CHCH$_2$SH
           |
           S—
48.7 —SCH$_2$$\underline{C}$HCH$_2$SH
           |
           S—

(Production of Plastic Lens)

52 parts by weight of m-xylylene diisocyanate, 0.015 parts by weight of dibutyltin dichloride as a curing catalyst, 0.10 parts by weight of ZELEC UN (trade name, product of Stepan Company; acidic phosphoric acid ester), and 0.05 parts by weight of BIOSORB 583 (manufactured by Kyodo chemical Co., Ltd.; ultraviolet absorbent) were mixed and dissolved at 20° C. 48 parts by weight of the polythiol compound containing 4-mercaptomethyl-1,8-dimercapto-3,6-dithiaoctane as a main component thus obtained was introduced and mixed, and thus a mixed uniform solution was obtained. This uniform solution was subjected to defoaming for 1 hour at 600 Pa, and then the uniform solution was filtered using a 1 μm TEFLON (registered trademark) filter. Subsequently, the filtered solution was injected into a mold formed from a glass mold and a tape. This mold was introduced into an oven, the temperature was slowly increased from 10° C. to 120° C., and polymerization was carried out for 20 hours. After completion of the polymerization, the mold was taken out from the oven, and a resin was obtained by releasing the product from the mold. The resin thus obtained was further subjected to annealing for 3 hours at 120° C. The properties of the lens thus obtained are shown in Table-2.

Examples A-2 to A-10

Polythiol compounds containing 4-mercaptomethyl-1,8-dimercapto-3,6-dithiaoctane as a main component were respectively produced in the same manner as in Example A-1, except that the production conditions described in Table-1 were used. The properties of the polythiol compounds thus obtained are shown in Table-1. Furthermore, the viscosities after 7 hours of the polymerizable compositions were measured, and plastic lenses were produced, in the same manner as in Example A-1. The results are shown in Table-2.

Example B-1

Synthesis of Polythiol Containing 4-mercaptomethyl-1,8-dimercapto-3,6-dithiaoctane as Main Component In a reactor, 124.6 parts by weight of 2-mercaptoethanol and 18.3 parts by weight of degassed water (dissolved oxygen concentration: 2 ppm) were introduced. 101.5 parts by weight of a 32 wt % aqueous solution of sodium hydroxide was added dropwise thereto over 40 minutes at 12° C. to 35° C., and then 73.6 parts by weight of epichlorohydrin was added dropwise thereto over 4.5 hours at 28° C. to 36° C. Subsequently, the mixture was stirred for 40 minutes. Production of 1,3-bis(2-hydroxyethylthio)-2-propanol was confirmed from NMR data.

Next, 183.7 parts by weight of thiourea having a purity of 99.90% was introduced, and 108.6 parts by weight of hydrogen chloride gas having a purity of 90.7% was blown therein. The mixture was stirred for 3 hours under reflux at 110° C., and thereby a reaction which forms thiuronium salt was carried out. The reaction mixture was cooled to 45° C., and then 320.5 parts by weight of toluene was added thereto, and the mixture was cooled to 31° C. 216.7 parts by weight of a 25 wt % aqueous ammonia solution was introduced over 29 minutes at 31° C. to 40° C., and a hydrolytic reaction was carried out by aging the mixture for 3 hours at 54° C. to 63° C. Thus, a toluene solution of a polythiol containing 4-mercaptomethyl-1,8-dimercapto-3,6-dithiaoctane as a main component was obtained. 162.9 parts by weight of 35.5% hydrochloric acid was added to the toluene solution, and thus the toluene solution was acid washed for 1 hour at 34° C. to 43° C. 174.2 parts by weight of degassed water (dissolved oxygen concentration: 2 ppm) was added thereto, and washing for 30 minutes at 35° C. to 45° C. was carried out two times. 162.8 parts by weight of 0.1% aqueous ammonia was added thereto, and washing was carried out for 30 minutes. 174.2 parts by weight of degassed water (dissolved oxygen concentration: 2 ppm) was added thereto, and washing for 30 minutes at 34° C. to 45° C. was carried out two times. Toluene and a trace amount of water were removed under heating at reduced pressure, and then the residue was filtered under reduced pressure using a 1.2 μm PTFE type membrane filter, and thus 205.0 parts by weight of a polythiol compound containing 4-mercaptomethyl-1,8-dimercapto-3,6-dithiaoctane as a main component was obtained. The properties of the polythiol compound thus obtained are shown in Table-1. Measurement of the viscosity of the polymerizable composition was carried out in the same manner as in Example A-1. The results are shown in Table-2.

Identification of 4-mercaptomethyl-1,8-dimercapto-3,6-dithiaoctane was carried out in the same manner as in Example A-1, and the same results were obtained.

(Production of Plastic Lens)

52 parts by weight of m-xylylene diisocyanate, 0.015 parts by weight of dibutyltin dichloride as a curing catalyst, 0.10 parts by weight of ZELEC UN (trade name, product of Stepan Company; acidic phosphoric acid ester), and 0.05 parts by weight of BIOSORB 583 (manufactured by Kyodo chemical Co., Ltd.; ultraviolet absorbent) were mixed and dissolved at 20° C. 48 parts by weight of the polythiol compound containing 4-mercaptomethyl-1,8-dimercapto-3,6-dithiaoctane as a main component thus obtained was introduced and mixed thereto, and thus a mixed uniform solution was obtained. This uniform solution was subjected to defoaming for 1 hour at 600 Pa, and then the uniform solution was filtered using a 1 μm TEFLON (registered trademark) filter. Subsequently, the filtered solution was injected into a mold formed from a glass mold and a tape. This mold was introduced into an oven, the temperature was slowly increased from 10° C. to 120° C., and polymerization was carried out for 20 hours. After completion of the polymerization, the mold was taken out from the oven, and a resin was obtained by releasing the product from the mold. The resin thus obtained was further subjected to annealing for 3 hours at 120° C. The properties of the lens thus obtained are shown in Table-2.

Examples B-2 to B-10

Polythiol compounds containing 4-mercaptomethyl-1,8-dimercapto-3,6-dithiaoctane as a main component were respectively produced in the same manner as in Example B-1, except that the production conditions described in Table-1 were used. The properties of the polythiol compounds thus obtained are shown in Table-1. Furthermore, the viscosities after 7 hours of the polymerizable compositions were measured, and plastic lenses were produced, in the same manner as in Example B-1. The results are shown in Table-2.

TABLE 1

|  | Condition I | Condition II | | Condition III | | Monomer analysis values | | | | | | |
|---|---|---|---|---|---|---|---|---|---|---|---|---|
|  | Reaction temperature °C. | Feed temperature °C. | Feed time minutes | Acid concentration % | Acid washing temperature °C. | Color | Specific gravity | Acidity ppm | Water ppm | Viscosity mPa·s | Refractive index | NH4 ppm |
| Example A-1 | 29-36 | 31-41 | 44 | 35.5 | 35-43 | 10 | 1.257 | 10 | 70 | 32 | 1.6310 | 0.02 |
| Example A-2 | 28-39 | 31-41 | 52 | 35.5 | 34-40 | 10 | 1.256 | 10 | 30 | 33 | 1.6308 | 0.01 |
| Example A-3 | 29-39 | 31-41 | 42 | 35.5 | 34-43 | 10 | 1.256 | 12 | 50 | 34 | 1.6308 | 0.02 |
| Example A-4 | 28-36 | 31-41 | 56 | 35.5 | 35-44 | 10 | 1.257 | 11 | 60 | 33 | 1.6309 | 0.05 |
| Example A-5 | 29-38 | 31-40 | 57 | 35.5 | 35-44 | 10 | 1.256 | 12 | 120 | 33 | 1.6308 | 0.05 |
| Example A-6 | 29-32 | 31-42 | 53 | 35.5 | 34-43 | 10 | 1.255 | 13 | 80 | 33 | 1.6310 | 0.06 |
| Example A-7 | 29-41 | 31-42 | 37 | 35.5 | 35-44 | 10 | 1.256 | 12 | 110 | 33 | 1.6309 | 0.04 |
| Example A-8 | 29-37 | 31-41 | 55 | 35.5 | 34-44 | 10 | 1.257 | 7 | 20 | 33 | 1.6312 | 0.02 |
| Example A-9 | 28-40 | 31-40 | 47 | 30 | 34-44 | 10 | 1.257 | 8 | 20 | 33 | 1.6312 | 0.02 |
| Example A-10 | 28-41 | 31-41 | 36 | 30 | 35-43 | 10 | 1.257 | 8 | 20 | 33 | 1.6313 | 0.03 |
| Example B-1 | 28-36 | 31-40 | 29 | 35.5 | 34-43 | 10 | 1.256 | 14 | 160 | 33 | 1.6312 | 0.04 |
| Example B-2 | 29-41 | 31-40 | 37 | 35.5 | 35-43 | 10 | 1.256 | 20 | 50 | 33 | 1.6315 | 0.01 |
| Example B-3 | 28-37 | 31-40 | 35 | 35.5 | 35-43 | 10 | 1.256 | 19 | 20 | 33 | 1.6311 | 0.02 |
| Example B-4 | 28-39 | 31-39 | 38 | 35.5 | 35-43 | 10 | 1.256 | 19 | 70 | 33 | 1.6309 | 0.02 |
| Example B-5 | 28-40 | 31-39 | 37 | 35.5 | 35-43 | 10 | 1.256 | 19 | 60 | 33 | 1.6306 | 0.01 |
| Example B-6 | 27-40 | 31-40 | 31 | 35.5 | 35-43 | 10 | 1.256 | 16 | 50 | 33 | 1.6309 | 0.01 |
| Example B-7 | 25-36 | 31-40 | 33 | 35.5 | 35-42 | 10 | 1.256 | 15 | 50 | 33 | 1.6309 | 0.04 |
| Example B-8 | 29-38 | 31-39 | 32 | 35.5 | 35-42 | 10 | 1.256 | 17 | 60 | 33 | 1.6309 | 0.04 |
| Example B-9 | 29-40 | 31-39 | 21 | 30 | 35-42 | 10 | 1.256 | 16 | 20 | 33 | 1.6312 | 0.02 |
| Example B-10 | 29-39 | 31-38 | 38 | 30 | 35-43 | 10 | 1.256 | 16 | 20 | 33 | 1.6313 | 0.01 |

Condition I: Reaction conditions for 2-mercaptoethanol and epichlorohydrin
Condition II: Feed conditions for the aqueous ammonia solution for the hydrolytic reaction
Condition III: Conditions for hydrochloric acid washing

TABLE 2

|  | Condition I | Condition II | | Condition III | | | Resin evaluation | | |
|---|---|---|---|---|---|---|---|---|---|
|  | Reaction temperature °C. | Feed temperature °C. | Feed time minutes | Hydrochloric acid concentration on acid washing % | Acid washing temperature °C. | Viscosity after 7 h (*) mPa·s | Color YI | Loss degree of transparency | Striation |
| Example A-1 | 29-36 | 31-41 | 44 | 35.5 | 35-43 | ○ | 4.2 | 15 | ○ |
| Example A-2 | 28-39 | 31-41 | 52 | 35.5 | 34-40 | ○ | 4.3 | 18 | ○ |
| Example A-3 | 29-39 | 31-41 | 42 | 35.5 | 34-43 | ○ | 4.3 | 18 | ○ |
| Example A-4 | 28-36 | 31-41 | 56 | 35.5 | 35-44 | ○ | 4.3 | 18 | ○ |
| Example A-5 | 29-38 | 31-40 | 57 | 35.5 | 35-44 | ○ | 4.0 | 17 | ○ |
| Example A-6 | 29-32 | 31-42 | 53 | 35.5 | 34-43 | ○ | 4.0 | 18 | ○ |
| Example A-7 | 29-41 | 31-42 | 37 | 35.5 | 35-44 | ○ | 3.9 | 17 | ○ |
| Example A-8 | 29-37 | 31-41 | 55 | 35.5 | 34-44 | ○ | 4.2 | 17 | ○ |
| Example A-9 | 28-40 | 31-40 | 47 | 30 | 34-44 | ○ | 4.2 | 17 | ○ |
| Example A-10 | 28-41 | 31-41 | 36 | 30 | 35-43 | ○ | 4.4 | 18 | ○ |
| Example B-1 | 28-36 | 31-40 | 29 | 35.5 | 34-43 | ○ | 4.4 | 17 | ○ |
| Example B-2 | 29-41 | 31-40 | 37 | 35.5 | 35-43 | ○ | 4.5 | 18 | ○ |

TABLE 2-continued

|  | Condition I | Condition II | Condition III | | | Resin evaluation | | |
|---|---|---|---|---|---|---|---|---|
|  | Reaction temperature °C. | Feed temperature °C. | Feed time minutes | Hydrochloric acid concentration on acid washing % | Acid washing temperature °C. | Viscosity after 7 h (*) mPa·s | Color YI | Loss degree of transparency | Striation |
| Example B-3 | 28-37 | 31-40 | 35 | 35.5 | 35-43 | o | 4.3 | 17 | o |
| Example B-4 | 28-39 | 31-39 | 38 | 35.5 | 35-43 | o | 4.2 | 18 | o |
| Example B-5 | 28-40 | 31-39 | 37 | 35.5 | 35-43 | o | 4.3 | 19 | o |
| Example B-6 | 27-40 | 31-40 | 31 | 35.5 | 35-43 | o | 4.3 | 18 | o |
| Example B-7 | 25-36 | 31-40 | 33 | 35.5 | 35-42 | o | 4.2 | 18 | o |
| Example B-8 | 29-38 | 31-39 | 32 | 35.5 | 35-42 | o | 4.3 | 18 | o |
| Example B-9 | 29-40 | 31-39 | 21 | 30 | 35-42 | o | 4.3 | 18 | o |
| Example B-10 | 29-39 | 31-38 | 38 | 30 | 35-43 | o | 4.3 | 19 | o |

Condition I: Reaction conditions for 2-mercaptoethanol and epichlorohydrin
Condition II: Feed conditions for the aqueous ammonia solution for the hydrolytic reaction
Condition III: Conditions for hydrochloric acid washing
(*) A sample having a viscosity after 7 hours of 250 mPa·s or less was rated as o, and a sample having a viscosity after 7 hours of 1000 mPa·s or more was rated as X.

Examples C-1 to C-12 and Comparative Examples A-1 to A-5

Polythiol compounds containing 4-mercaptomethyl-1,8-dimercapto-3,6-dithiaoctane as a main component were respectively produced in the same manner as in Example A-1, except that the production conditions described in Table-3 were used. The viscosities after 7 hours of the polymerizable compositions were measured, and plastic lenses were produced, in the same manner as in Example A-1. The results are shown in Table-3.

TABLE 3

|  | Condition I | Condition II | Condition III | | | Resin evaluation | | |
|---|---|---|---|---|---|---|---|---|
|  | Reaction temperature °C. | Feed temperature °C. | Feed time minutes | Hydrochloric acid concentration on acid washing % | Acid washing temperature °C. | Viscosity after 7 h (*) mPa·s | Color YI | Loss degree of transparency | Striation |
| Example C-1 | 29-31 | 32-41 | 33 | 35.5 | 37-42 | o | 4.4 | 18 | o |
| Example C-2 | 47-50 | 32-43 | 32 | 35.5 | 38-43 | o | 4.2 | 19 | o |
| Example C-3 | 27-29 | 15 | 35 | 35.5 | 36-40 | o | 4.4 | 19 | o |
| Example C-4 | 26-31 | 37-40 | 38 | 35.5 | 35-39 | o | 4.4 | 18 | o |
| Example C-5 | 28-30 | 51-55 | 35 | 35.5 | 37-44 | o | 4.3 | 19 | o |
| Example C-6 | 26-29 | 32-43 | 32 | 35.5 | 18-22 | o | 4.3 | 20 | o |
| Example C-7 | 27-29 | 32-43 | 10 | 35.5 | 38-43 | o | 4.4 | 18 | o |
| Example C-8 | 26-30 | 31-42 | 60 | 35.5 | 37-42 | o | 4.4 | 20 | o |
| Example C-9 | 28-33 | 33-42 | 80 | 35.5 | 36-40 | o | 4.4 | 23 | o |
| Example C-10 | 27-31 | 31-40 | 29 | 25.0 | 36-43 | o | 4.1 | 17 | o |
| Example C-11 | 27-29 | 32-40 | 35 | 35.5 | 11-14 | o | 4.4 | 18 | o |
| Example C-12 | 26-30 | 24-25 | 30 | 35.5 | 35-41 | o | 4.1 | 18 | o |
| Comparative Example A-1 | 8-9 | 33-42 | 31 | 35.5 | 35-39 | o | 5.3 | 20 | o |
| Comparative Example A-2 | 26-32 | 63-65 | 34 | 35.5 | 34-41 | o | 5.1 | 20 | o |
| Comparative Example A-3 | 27-29 | 32-40 | 120 | 35.5 | 33-40 | o | 5.0 | 20 | o |
| Comparative Example A-4 | 27-30 | 32-40 | 28 | 20.0 | 34-39 | x | 3.9 | 17 | x |
| Comparative Example A-5 | 26-30 | 31-40 | 31 | 35.5 | 53-57 | o | 5.1 | 26 | o |

Condition I: Reaction conditions for 2-mercaptoethanol and epichlorohydrin
Condition II: Feed conditions for the aqueous ammonia solution for the hydrolytic reaction
Condition III: Conditions for hydrochloric acid washing
(*) A sample having a viscosity after 7 hours of 250 mPa·s or less was rated as o, and a sample having a viscosity after 7 hours of 1000 mPa·s or more was rated as X.

As discussed above, high quality plastic lenses were obtained by using the polythiol compounds of Examples. On the other hand, in Comparative Examples, there was a problem with at least one of color, loss degree of transparency, and striation, so that plastic lenses having satisfactory quality were not obtained.

Furthermore, the polymerizable composition containing the polythiol compound of Comparative Example A-4 had a viscosity after 7 hours of 1000 mPa·s or more, and thus it was made clear that the production stability of plastic lenses was affected thereby.

At the time of actual production, it is necessary to consider that the volume efficiency (inconvenience such as precipitation during operation), stirrability, and a cooling operation may be needed when the operation temperature is too low as compared with the preceding process. From this viewpoint, in regard to Conditions II (introduction of aqueous ammonia at the time of the hydrolytic reaction), it is preferable to select the operation temperature to be 15° C. or higher, and in regard to Conditions III (hydrochloric acid washing), it is preferable to select the operation temperature to be 10° C. or higher.

From the above results, it was made clear that when a polythiol compound obtained by allowing 2-mercaptoethanol to react with an epihalohydrin compound at a temperature of 10° C. to 50° C. under Conditions I; adding aqueous ammonia within 80 minutes while maintaining the reaction liquid at a temperature of 15° C. to 60° C. to hydrolyze an isothiuronium salt under Conditions II; adding hydrochloric acid at a concentration of 25% to 36% to a solution containing a polythiol compound; washing the solution at a temperature of 10° C. to 50° C.; and thereby purifying the polythiol compound under Conditions III, is used, a plastic lens formed from a polythiourethane-based resin having excellent quality such as color, transparency, and striation can be produced. Furthermore, according to the present invention, it was made clear that even in the case where a polythiol compound is repeatedly produced in the production in an actual industrial scale, plastic lenses having a desired product quality are stably obtained without any fluctuation in the product quality of the polythiol compound between different production batches.

This application claims priority from Japanese Patent Application No. 2012-179896 filed Aug. 14, 2012, the entire disclosure of which is incorporated herein by reference.

The invention includes the following embodiments.

[a1] A method for producing a polythiol compound, comprising:
a step for reacting a polyalcohol compound with thiourea in the presence of hydrogen chloride to obtain an isothiuronium salt; and
a step for adding, while maintaining a reaction solution containing the isothiuronium salt thus obtained at a temperature of 20° C. to 60° C., aqueous ammonia to the reaction solution within 80 minutes, thereby hydrolyzing the isothiuronium salt to obtain a polythiol compound.

[a2] The method for producing a polythiol compound according to [a1], further including, after the step for hydrolyzing the isothiuronium salt to obtain a polythiol compound,
a step for adding hydrochloric acid which is a concentration of 25% to 36% to the solution containing the polythiol compound thus obtained, washing the solution at a temperature of 20° C. to 50° C. to purify the polythiol compound.

[a3] The method for producing a polythiol compound according to [a1] or [a2], further including, before the step for reacting the polyalcohol compound with thiourea to obtain an isothiuronium salt,
a step for reacting 2-mercaptoethanol with an epihalohydrin compound represented by the following formula (1) at a temperature of 2° C. to 50° C. to obtain a polyalcohol compound represented by the following formula (2).

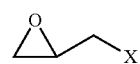

(wherein X represents a halogen atom)

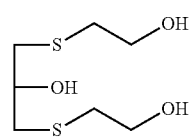

[a4] The method for producing a polythiol compound according to [a3], wherein the step for reacting 2-mercaptoethanol with an epihalohydrin compound includes
a step for reacting 2-mercaptoethanol with an epihalohydrin compound represented by the following formula (1) at a temperature of 2° C. to 20° C., and thereby obtaining a compound represented by the following formula (3); and

(wherein X represents a halogen atom)

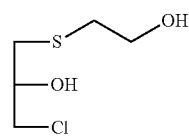

a step for reacting the compound represented by formula (3) with 2-mercaptoethanol at a temperature of 10° C. to 50° C. to obtain a polyalcohol compound represented by the following formula (2).

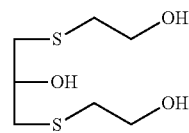

[a5] The method for producing a polythiol compound according to [a3] or [a4], wherein the polythiol compound is 4-mercaptomethyl-1,8-dimercapto-3,6-dithiaoctane.

[a6] The method for producing a polythiol compound according to [a1] or [a2], further including, before the step for reacting the polyalcohol compound with thiourea to obtain an isothiuronium salt, a step for reacting 2-mercaptoethanol with an epihalohydrin compound represented by the following formula (1) at a temperature of 2° C. to 20° C., and thereby obtaining a compound represented by the following formula (3); and

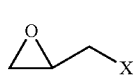     (1)

(wherein X represents a halogen atom)

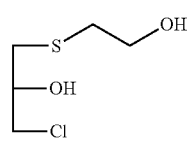     (3)

a step for reacting the compound represented by formula (3) with sodium sulfide to obtain a polyalcohol compound represented by the following formula (4).

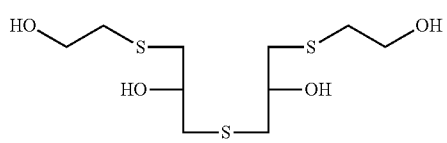     (4)

[a7] The method for producing a polythiol compound according to [a6], wherein the polythiol compound includes one kind or two or more kinds selected from the group consisting of 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane.

[a8] A method for industrial manufacture of a polythiol compound, using the method according to any one of [a1] to [a7].

[a9] A polymerizable composition for optical materials, comprising a polythiol compound obtained by the method according to any one of [a1] to [a8].

[a10] A molded product obtained by curing the polymerizable composition for optical materials according to [a9].

[a11] A plastic lens comprising the molded product according to [a10].

The invention claimed is:

1. A method for producing a molded product, comprising:
a step for preparing a polymerizable composition for optical materials and a step for curing the polymerizable composition for optical materials to produce the molded product;
wherein the step for preparing the polymerizable composition for optical materials comprises a step for preparing a polythiol compound represented by the following formula (5), and a step for preparing the polymerizable composition for optical materials from the polythiol compound represented by the following formula (5);

wherein the step for preparing the polythiol compound represented by the following formula (5) comprises:
a step for reacting 2-mercaptoethanol with an epihalohydrin compound represented by the following formula (1) at a temperature of 10° C. to 50° C. to obtain a polyalcohol compound represented by the following formula (2);

     (1)

(wherein X represents a halogen atom)

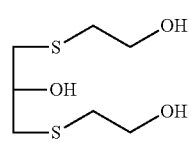     (2)

a step for reacting the polyalcohol compound represented by formula (2) thus obtained with thiourea in the presence of hydrogen chloride to obtain an isothiuronium salt;
a step for adding, while maintaining a reaction solution containing the isothiuronium salt thus obtained at a temperature of 15° C. to 60° C., aqueous ammonia to the reaction solution within 80 minutes, thereby hydrolyzing the isothiuronium salt to obtain a polythiol compound represented by the following formula (5); and

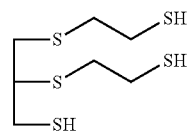     (5)

a step for adding hydrochloric acid which is a concentration of 25% to 36% to the solution containing the polythiol compound thus obtained, washing the solution at a temperature of 10° C. to 50° C. to purify the polythiol compound represented by the formula (5).

2. The method for producing a molded product according to claim 1,
wherein the step for reacting 2-mercaptoethanol with the epihalohydrin compound comprises:
a step for reacting 2-mercaptoethanol with the epihalohydrin compound represented by formula (1) at a temperature of 10° C. to 20° C. to obtain a compound represented by the following formula (3); and

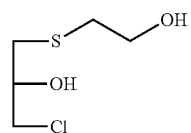     (3)

a step for reacting the compound represented by formula (3) with 2-mercaptoethanol at a temperature of 10° c. to 50° C. to obtain the polyalcohol compound represented by formula (2).

3. The method for producing a molded product according to claim 1,
   wherein the polymerizable composition for optical materials further comprises a polyiso(thio)cyanate compound.

4. The method for producing a molded product according to claim 2,
   wherein the polymerizable composition for optical materials further comprises a polyiso(thio)cyanate compound.

* * * * *